US012620090B2

(12) United States Patent
Chu et al.

(10) Patent No.: US 12,620,090 B2
(45) Date of Patent: May 5, 2026

(54) ANALYSIS OF FUNDUS AUTOFLUORESCENCE IMAGES

(71) Applicant: Verana Health, Inc., San Francisco, CA (US)

(72) Inventors: Zhongdi Chu, San Francisco, CA (US); Aishwarya Ramakrishnan, Shrewsbury, MA (US); Kim Ngoc Le, South San Francisco, CA (US); Ketki Suresh Khapare, Richardson, TX (US); Carlos Gutierrez Candano, Austin, TX (US)

(73) Assignee: VERANA HEALTH, INC., San Francisco, CA (US)

( * ) Notice: Subject to any disclaimer, the term of this patent is extended or adjusted under 35 U.S.C. 154(b) by 246 days.

(21) Appl. No.: 18/198,227

(22) Filed: May 16, 2023

(65) Prior Publication Data

US 2024/0386546 A1 Nov. 21, 2024

(51) Int. Cl.
*G06T 7/00* (2017.01)
*G16H 30/20* (2018.01)
*G06N 3/02* (2006.01)

(52) U.S. Cl.
CPC ........... *G06T 7/0012* (2013.01); *G16H 30/20* (2018.01); *A61B 2576/00* (2013.01); *G06N 3/02* (2013.01); *G06T 2207/10064* (2013.01); *G06T 2207/30041* (2013.01)

(58) Field of Classification Search
None
See application file for complete search history.

(56) References Cited

U.S. PATENT DOCUMENTS

| 12,112,480 | B2 * | 10/2024 | Boyd | A61B 3/12 |
| 2014/0276025 | A1 * | 9/2014 | Durbin | A61B 3/0025 |
| | | | | 600/407 |
| 2015/0002813 | A1 * | 1/2015 | Ota | A61B 3/12 |
| | | | | 351/246 |

(Continued)

OTHER PUBLICATIONS

Bearelly, Srilaxmi, "Use of Fundus Autofluorescence Images to Predict Geographic Atrophy Progression", Retina 31 1, (Jan. 2011), 12 pages.

(Continued)

*Primary Examiner* — Haris Sabah
(74) *Attorney, Agent, or Firm* — SCHWEGMAN LUNDBE4RG & WOESSNER, P.A.

(57) ABSTRACT

Systems and methods herein provide analysis of fundus autofluorescence (FAF) images. A set of FAF images are received, each FAF image in the set of FAF images containing at least a portion of an eye of a patient. Each FAF image in the set of FAF images is processed by generating a set of features based on the FAF image, applying the set of features to a deep learning model to determine a gradeability status of the FAF image, and responsive to determining the FAF image is gradable, applying the set of features to a machine-learned model to determine a quality score for the FAF image. Responsive to processing each FAF image in the set of FAF images, a highest quality gradable FAF image of the patient is determined, where the highest quality gradable FAF image is the FAF image having the highest quality score.

20 Claims, 10 Drawing Sheets

(56)                    References Cited

U.S. PATENT DOCUMENTS

| 2016/0345819 | A1* | 12/2016 | Jayasundera | ............. | G06T 7/12 |
| 2023/0154595 | A1* | 5/2023 | Gao | ...................... | G16H 50/20 |
| | | | | | 382/128 |

OTHER PUBLICATIONS

Bindewald-Wittich, Almut, "Blue-light fundus autofluorescence imaging of pigment epithelial detachments", Eye Lond 37, (Apr. 2023), 11 pages.

Chakroborty, Sandipan, "Image quality assessment of ultra-widefield fundus images using deep convolutional neural networks.", ARVO Imaging in the Eye Conference Abstract, (Aug. 2019), 4 pages.

Huang, Natalie T., "Comparing fundus autofluorescence and infra-red imaging findings of peripheral retinoschisis, schisis detachment, and retinal detachment", American Journal of Ophthalmology Case Reports 18, (Mar. 26, 2020), 6 pages.

Manivannan, Niranchana, "Deep learning based GA segmentation in fundus autofluorescence images", ARVO Annual Meeting Abstract, (Jul. 2019), 3 pages.

Schmitz-Valckenberg, Steffen, "Fundus Autofluorescence Imaging Review and Perspectives", Retina 28 3 Abstract Only, (Mar. 2008), 2 pages.

Shagam, Taylor, "Deep learning based binary image quality algorithm for low-cost fundus imaging system in remote care settings", ARVO Annual Meeting Abstract, (Jun. 2021), 5 pages.

* cited by examiner

300

302  ACCESS A FAF IMAGE FROM A SET OF FAF IMAGES

304  PROCESS THE FAF IMAGE

306  CAUSE DISPLAY OF A PRESENTATION OF THE FAF
IMAGE BASED ON PROCESSING OF THE FAF IMAGE

302

304

308 — DETERMINE A SET OF FEATURES BASED ON THE FAF IMAGE

310 — DETERMINE A GRADEABILITY STATUS OF THE FAF IMAGE ASSOCIATED WITH THE SET OF FEATURES

312 — GRADEABLE

YES

NO

314 — DETERMINE A QUALITY SCORE FOR THE FAF IMAGE ASSOCIATED WITH THE SET OF FEATURES

306

300

302

304

316

QUALITY SCORE EXCEEDS A
THRESHOLD VALUE

318

NO

PROMPT A USER TO RE-
CAPTURE THE FAF
IMAGE

YES

306

300

302

304

320
QUALITY SCORE EXCEEDS A
CLINICAL TRIAL
THRESHOLD

322

YES

PROMPT TO INCLUDE PATIET IN
CLINICAL TRIAL

NO

324

PROMPT TO EXCLUDE PATIENT FROM
CLINICAL TRIAL

306

ANALYSIS OF FUNDUS AUTOFLUORESCENCE IMAGES

BACKGROUND

Ophthalmic images are routinely used in clinical practice and clinical research for various ocular diseases. For many severe ocular diseases, including various end-stage macular degeneration, such as geographic atrophy, ophthalmic images such as fundus autofluorescence (FAF) images are commonly used to diagnose and track disease progression. When interpreting ophthalmic images, it is important for the images to be of sufficient image quality to avoid incorrect interpretation and annotation, which can cause delayed or incorrect disease diagnosis, patient mismanagement in clinical practice, failed patient screening, and/or wasted resources in clinical trials and clinical research.

FAF imaging is a non-invasive imaging modality that has become increasingly popular in both clinical research and clinical practice settings due to its ability to map naturally and pathologically occurring fluorophores in the posterior segment. FAF imaging is particularly useful in the diagnosis and management of retinal dystrophies, including but not limited to geographic atrophy, choroidal dystrophies, retinitis pigmentosa, and other similar ocular diseases.

For example, in geographic atrophy clinical trials, FAF images are used to screen patients suitable for the clinical trial as well as to measure geographic atrophy lesion size changes as the primary efficacy endpoint. Conventionally, FAF images collected in clinical trials are interpreted manually by highly specialized graders in a central reading center. The highly specialized graders review FAF images and determine whether they are high enough quality to be gradable. This time-consuming and resource-intensive manual process is possible in clinical trial settings, but is not scalable to real-world medical practice settings. This approach also relies heavily on subjective human judgement, making it prone to human error and bias.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Systems and methods presented herein provide a means for FAF image quality analysis to aide in diagnosis and evaluation in clinical settings, including clinical trials. In a two-step approach, a FAF image is first processed to determine a gradeability status by a gradeability model, such as a deep learning model trained to determine a gradeability status. The gradeability model performs analysis conventionally performed by the highly specialized graders. The gradeability status can be "gradable" or "non-gradable," according to exemplary embodiments. A non-gradable image is not analyzed further. A gradable image is further analyzed by a quality model. The quality model, such as a machine-learned model trained to determine image quality, performs additional processing to provide a quality score, which quantifies the quality of the FAF image.

The FAF image and analysis results, including gradeability status and, if applicable, quality score, are provided for display in a presentation. The presentation may contain other information to aide a clinician. For example, the presentation can indicate whether the FAF image is of sufficient quality for clinical use, and if not, prompt the clinician to re-capture the image before the patient associated with the FAF image leaves the clinical setting, thereby improving efficiency of providing healthcare. Additionally or alternatively, the presentation can include whether the patient qualifies for inclusion in a particular clinical trial based on the FAF image analysis results. Moreover, in the event the FAF image is one of a set of multiple FAF images associated with the same patient on the same day, the presentation may determine the FAF image with the highest quality score and prompt clinicians to use the highest quality score image in the clinical setting.

Figure 1:
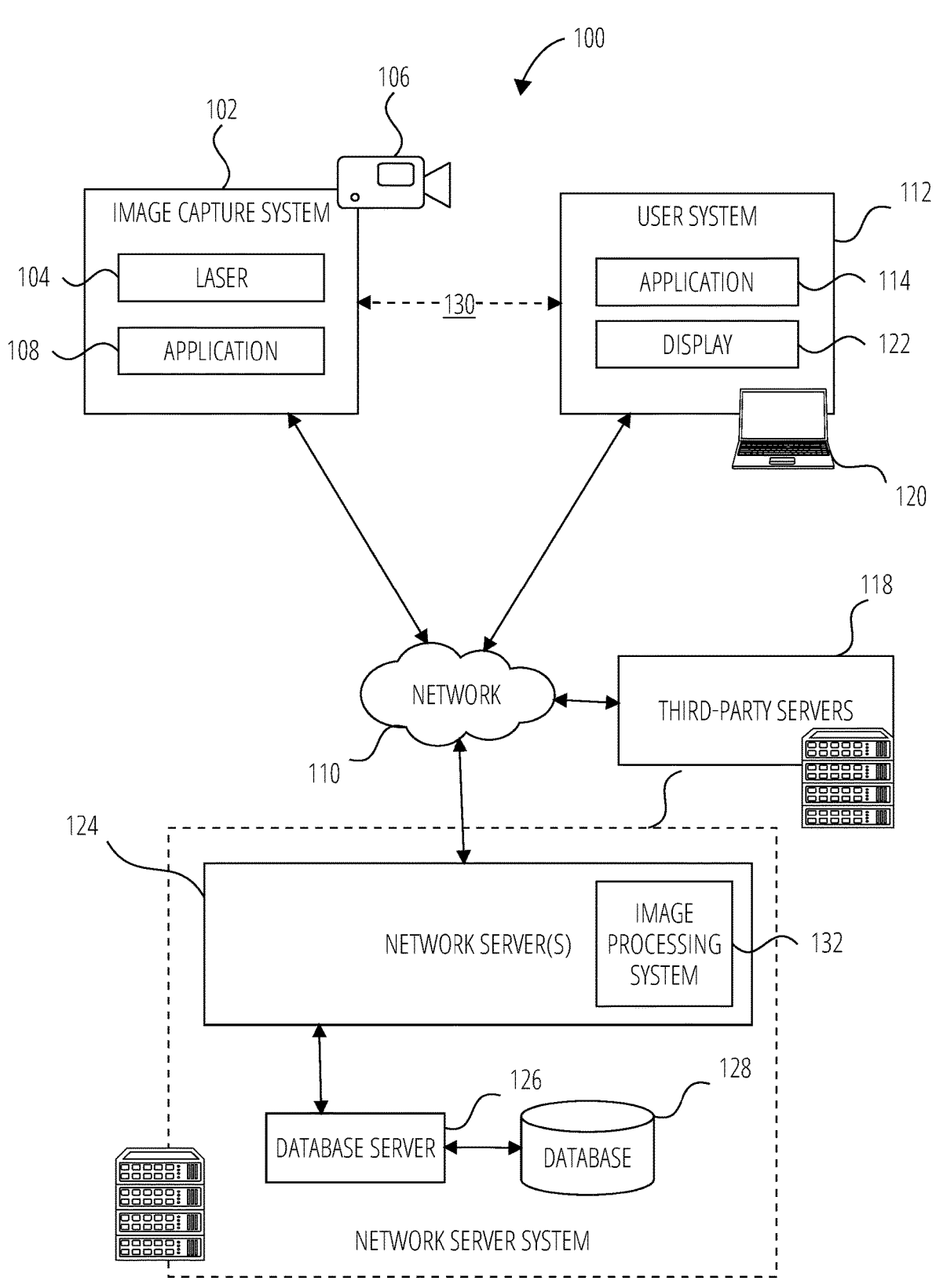
FIG. 1 is a diagrammatic representation of a networked environment in which the present disclosure may be deployed, according to some examples.

FIG. 1 is a block diagram showing an example system 100 for capturing, analyzing, storing, and using FAF image(s) over a network. The system 100 includes at least an image capture system 102 configured to capture one or more FAF images. The image capture system 102 includes a laser 104 and a camera 106.

Fluorophores are molecules or materials that possess fluorescent properties when exposed to electromagnetic radiation (i.e., light) of one or more particular wavelength ranges, termed autofluorescence. The particular range of wavelengths depends on the chemical structure of the fluorophore. The fundus (i.e., interior surface) of an eye has a plurality of fluorophores, such as optic nerve drusen, astrocytic hamartomas, lipofuscin pigments in the retina, and crystalline lenses. FAF imaging captures the autofluorescence of one or more of these structures in an eye while the eye is illuminated by electromagnetic radiation of one or more particular wavelength ranges. For example, the camera 106 captures one or more FAF images of an eye while the laser 104 irradiates the eye.

The laser 104 is configured to provide electromagnetic radiation in one or more specific ranges of wavelength. Wavelengths in the visual spectrum, particular blue and green wavelengths, and/or near-infrared wavelengths are typically used for FAF imaging. For example, to capture lipofuscin the laser 104 may be configured to emit light of wavelengths ranging from 500 nm to 750 nm.

The camera 106 is configured to capture one or more images of the fundus of the eye while the laser 104 is illuminating the fundus. The laser 104 may be configured to provide a flash of light when the camera 106 is taking an image. The camera 106 may include one or more filters to provide better contrast in images. For example, a filter may be used to block out red wavelengths. The camera 106 may be configured to capture images in color and/or black and white.

The laser 104 and camera 106 may be integrated into one apparatus. In one example, the laser 104 and the camera 106 are integrated into a free-standing or tabletop fundus camera-based system that a patient gazes into during image capture. In another example, the laser 104 and the camera 106 are integrated into an ophthalmoscope, such as a scanning laser ophthalmoscope (SLO), a confocal scanning laser ophthalmoscope (cSLO), or an ultra-widefield confocal scanning laser ophthalmoscope (uwcSLO), according to some examples. The cSLO provides benefits such as a narrow range of wavelengths for efficient excitation of relevant fluorophores, as well as reduced noise and increased exposure. The uwcSLO provides benefits such as capturing a larger span of the fundus in one image.

The image capture system 102 optionally includes an application 108 that provides processing of FAF images captured by the camera 106. According to some examples, the application 108 is configured to communicate with a network 110 using one or more application program interface(s) (APIs). For example, the application 108 enables interactions between the image capture system 102 and a user system 112.

The system 100 includes at least one user system 112, each of which may host multiple applications, including an application 114. Each user system 112 is communicatively coupled, via a network 110 (e.g., the Internet), to the image capture system 102, a network server system 116 and third-party server 118. Each user system 112 may include one or more user devices, such as a computer client device 120 that are communicatively connected to the network 110 to exchange data.

The application 114 provides processing and enables communication with the network 110 through one or more APIs. The application 114 may be the same instance as or another instance of the application 108 in embodiments where the user system 112 is integrated into the image capture system 102 (e.g., the computer client device 120 is used as part of the image capture system 102). That is, the image capture system 102 is optionally directly connected 130 to at least one user system 112.

The user system 112 includes a display 122 configured to display a user interface. The display 122 may be integrated into the one or more user devices, such as the computer client device 120.

The image capture system 102 interacts with a user system 112 and with the network server system 116 via the network 110. The data exchanged between the image capture system 102 and one or more user system 112 and the network server system 116 includes functions (e.g., commands to invoke functions) and payload data (e.g., text, audio, video, or other multimedia data).

The network server system 116 provides server-side functionality via the network 110 to the image capture system 102 and the user system 112. While certain functions of the system 100 are described herein as being performed by either the application 108, the application 114, or by the network server system 116, the location of certain functionality either within the application 108, the application 114, or the network server system 116 may be a design choice. For example, it may be technically preferable to initially deploy particular technology and functionality within the network server system 116 but to later migrate this technology and functionality to the application 114 where a user system 112 has sufficient processing capacity.

The network server system 116 supports various services and operations that are provided to the application 108 and/or application 114. Such operations include transmitting data to, receiving data from, and processing data generated by the image capture system 102. This data may include one or more FAF images, patient information, configurations of the image capture system 102, client device information, geolocation information, and other metadata. Data exchanges within the system 100 are invoked and controlled through functions available via user interfaces (UIs) of the application 108 and/or application 114.

The network server system 116 includes one or more network servers 124 that provide processing functionality, making the functions of the network servers 124 accessible to the application 108 of the image capture system 102, other applications 114 and third-party server 118. The network servers 124 are communicatively coupled to a database server 126, facilitating access to a database 128 that stores data associated with interactions processed by the network servers 124. Similarly, the network servers 124 provides web-based interfaces and APIs, according to some examples. To this end, the network servers 124 process incoming network requests over the Hypertext Transfer Protocol (HTTP) and several other related protocols.

The network server system 116 receives and transmits interaction data (e.g., commands and data payloads) between the network servers 124 and the clients (for example, the application 108 and the application 114) and the third-party server 118. Specifically, the network server system 116 provides a set of interfaces (e.g., routines and protocols) that can be called or queried to invoke functionality of the network servers 124. The network server system 116 exposes various functions supported by the network servers 124, including account registration; login functionality; the sending of data, via the network servers 124, from a particular user system 112; the communication of files (e.g., images or other data) from the image capture system 102 to the network servers 124; the metadata of a collection of data (e.g., patient information); the storage or retrieval of a data (e.g., FAF images) from the database 128.

The network servers 124 host multiple systems and subsystems, including an image processing system 132 described below with reference to FIG. 2. The functionality of the image processing system 132 is described herein may be partially or fully performed on each of the application 108 of the image capture system 102 or application 114 of an instance of the user system 112. Description of the image processing system 132 in reference to the network server system 116 is not meant to be limiting.

Figure 2:
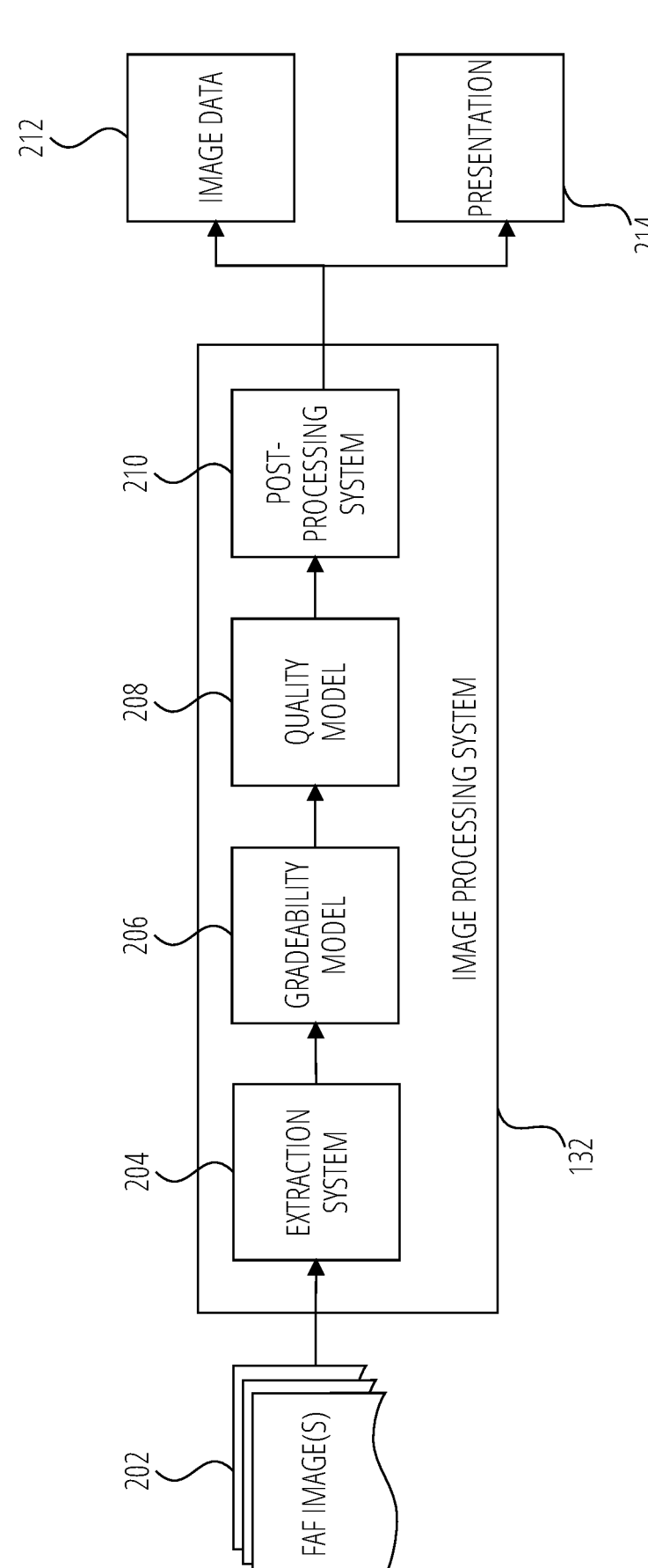
FIG. 2 is a diagrammatic representation of an image processing system, according to some examples.

FIG. 2 is a diagrammatic representation of an image processing system 132, according to some examples. The image processing system 132 processes FAF images 202 to analyze the quality thereof. The image processing system 132 receives one or more FAF images 202 of the fundus of an eye of a patient exhibiting autofluorescence. For example, a clinician may have captured a plurality of FAF images 202 of the patient on a single day. According to some examples, the FAF images 202 are in the Digital Imaging and Communications in Medicine (DICOM) format, or other common image formats such as PNG, JPEG, BMP, or other raster image formats.

According to some examples, the FAF images 202 are captured by the image capture system 102 and transmitted to the network server system 116 via the network 110. The network server system 116 stores the FAF images 202 in the database 128. The image processing system 132 accesses the FAF images 202 in the database 128, or otherwise receives the images from the database 128 or image capture system 102.

The image processing system 132 includes an extraction system 204 that determines a set of features derived from a FAF image 202. The extraction system 204 receives the one or more FAF images 202 According to some examples, the extraction system 204 extracts metadata from the FAF image 202 and extracts a pixel array from the FAF image 202. That is, according to some examples, the set of features includes the metadata and the pixel array. The metadata includes information about the FAF image 202, such as patient information, temporal information (e.g., date and time), and information about the image capture system 102. The pixel array is a data representation of the pixels that comprise the FAF image 202.

The extraction system 204, additionally or alternatively, determines a set of local features and/or a set of global features, according to some examples. The global features determine quality metrics for the whole FAF image 202. The local features determine quality metrics from different patches of the FAF image 202. Each patch comprises a portion of the FAF image 202, and patches may be of differing sizes and may overlap one another. The extraction system 204 determines a set of patches. According to some examples, the extraction system 204 selects at least some of the patches in the set of patches based on identification of anatomical structures such as optical disc, macula, and vascular network(s). Local feature extraction can be complex and prone to errors. A hybrid approach that extracts both global features and local features is more robust and less prone to error.

The local and/or global features determined by the extraction system 204 represent one or more quality metrics. According to some examples, the one or more quality metrics include one or more of the list comprising: signal intensity, noise, contrast, and blurriness. For example, the extraction system 204 segments the FAF image 202 (or a patch thereof) into a vascular-and-atrophic region and a non-vascular-and-non-atrophic region. The signal intensity corresponds to a calculated mean pixel intensity of the mean pixel intensity of the non-vascular-and-non-atrophic region. Noise is determined, for example, as the zero-mean additive Gaussian noise (e.g., similar to speckle noise). Contrast is calculated as the ratio of average signal intensity of the non-vascular-and-non-atrophic and the average signal intensity of the vascular-and-atrophic region. Blurriness is calculated as the aggregate of blur metrics along all axes of the FAF image 202 (or the patch thereof).

The extraction system 204 may determine additional or alternative features from the FAF image 202. In instances where there are multiple FAF images in the set of FAF images 202, the extraction system 204 determines a set of features for each FAF image 202.

The image processing system 132 includes a gradeability model 206 that receives at least the set of features associated with the FAF image 202 from the extraction system 204. The gradeability model 206 determines, for each FAF image 202, a gradeability status of the FAF image 202. The gradeability status is one of "gradable" or "non-gradable," according to some examples. The gradeability model 206 determines the gradeability status of the FAF image 202 based on the set of features. The gradeability model 206 processes the set of features to determine the gradeability status, and may alter or add to the set of features in processing the set of features.

The gradeability model 206 is, for example, implemented as a deep-learning model that has been trained to determine a gradeability status of a FAF image 202 associated with a set of features. Training of an exemplary deep-learning model is described further in relation to FIG. 4. The gradeability model 206 automates and standardizes processes conventionally performed by highly trained graders. The gradeability model 206 is less prone to human error and biases and produces results that are standardized and reproducible.

A gradable FAF image 202 is of sufficient quality to undergo further analysis. A non-gradable FAF image 202 is not of sufficient quality to undergo further analysis. For example, a non-gradable image may be too blurry, over-exposed, or otherwise be unusable for clinical and diagnostic means. According to some examples, the image processing system 132 discards non-gradable FAF images 202. The gradeability model 206 prompts a user (e.g., a clinician) to re-capture a non-gradable FAF image 202, according to some examples.

The image processing system 132 includes a quality model 208 that determines a quality score for each gradable FAF image 202. The quality model 208 receives at least the set of features associated with the FAF image 202 and the gradeability status of the FAF image 202 from the gradeability model 206 The quality model 208 determines a quality score for the FAF image 202 based on the set of features, where the quality score indicates an overall level of quality of the FAF image 202. For example, the quality score spans a range of values wherein a low value indicates poor quality, and a high value indicates high quality. According to some examples, the quality score is a numeric value between zero and ten.

According to some examples, the quality model 208 does not process non-gradable FAF images 202 to determine a quality score. The quality model 208 may assign each non-gradable FAF image 202 the lowest quality score possible (e.g., zero if the range of quality scores is 0-10), according to some examples.

The quality model 208 is, for example, implemented as a machine-learned model that has been trained to determine a quality score of a FAF image 202 associated with a set of features. Training of an exemplary machine-learned model is described further in relation to FIG. 5A and FIG. 5B. The quality model 208 provides a novel means of quality analysis of gradable FAF images 202. The quality scores generated by the quality model 208 are a level of analysis beyond what conventional highly skilled graders produce. Furthermore, the quality model 208 automates and standardizes the quality analysis, enabling fast and reproducible results.

The image processing system 132 optionally includes a post-processing system 210. The post-processing system 210 is configured to perform one or more post-processing functions, such as generating image data 212 and generating a presentation 214. For example, the image data 212 includes the FAF image 202 and data generated by the image processing system 132, such as the gradeability status and the quality score. The image data 212 may be transmitted to the database server 126 for storage in the database 128. The image data 212 can be downloaded from the database 128, for example, in a CSV file.

The post-processing system 210 generates the presentation 214 of the FAF image 202 based on the quality score of the FAF image 202. The presentation 214 includes the image data 212 presented as a user interface (UI). According to some examples, the presentation 214 includes a display of the quality score at a position upon the FAF image 202. The presentation may include additional information or data, such as the metadata determined by the extraction system 204.

In instances where the image processing system 132 receives a set of FAF images 202, the post-processing system 210 may generate a presentation of the set of FAF images 202. For example, the presentation 214 includes a display of a particular FAF image 202 at a position among the set of FAF images 202. According to some examples, the post-processing system 210 determines a FAF image 202 with the highest quality score of the set of FAF images 202 and generates the presentation of the highest quality FAF image 202. For example, the post-processing system 210 may generate a UI to be displayed on a client device of a user (e.g., a clinician), the UI including the highest quality FAF image 202, the gradeability status of the highest quality FAF image 202, and the quality score of the highest quality FAF image 202.

The image processing system 132 automatically determining and presenting the highest quality FAF image 202 of a set of FAF images 202 has numerous benefits in a clinical setting. A clinician, such as a doctor, reviewing the presentation 214 on the user system 112 is automatically presented with the highest quality FAF image 202 for review. The clinician does not have to waste time determining which FAF image 202 in the set of FAF images 202 is the best; instead, the clinician can jump straight into diagnostic work. Similarly, the image processing system 132 can analyze FAF images 202 much more quickly than conventional highly skilled graders. Thereby helping patients to reach the step of a clinician's diagnostic review more quickly, to reach a diagnosis and treatment more quickly. In degenerative conditions, such as macular degeneration, faster diagnosis and treatment can prevent further irreversible vision loss.

The post-processing system 210 additionally or alternatively determines whether the quality score of a particular FAF image 202 exceeds a threshold value. For example, responsive to determining the quality score of the FAF image 202 exceeds the threshold value, the post-processing system 210 may generate and transmit a notification to the client device that includes the presentation 214 of the FAF image 202.

The threshold value may be a threshold quality score. For example, responsive to determining the quality score of a particular FAF image 202 is less than the threshold quality score, the post-processing system 210 prompts the user of the client device to recapture the FAF image 202 as part of the presentation 214. Additionally, or alternatively, in the event of determining the quality score of the highest quality FAF image 202 is less than the threshold quality score, the post-processing system 210 prompts the user of the client device to recapture the set of FAF images 202.

The threshold value may be a clinical trial threshold quality score. For example, the image processing system 132 may access data associated with one or more clinical trials from, for example, the database 128 or third-party servers 118. The data associated with a particular clinical trial may include a clinical trial threshold quality score. The clinical trial threshold quality score is a quality cutoff metric for inclusion in the associated clinical trial. In the event the quality score of a FAF image 202 exceeds the clinical trial threshold quality score, the post-processing system 210 prompts the user of the client device to include the patient in the clinical trial as part of the presentation 214. The presentation 214 may include additional information relating to the clinical trial, such as how to enroll the patient associated with the FAF image 202 in the clinical trial.

The presentation 214 generated by the post-processing system 210 can be transmitted with instructions to the user system 112 via the network 110. The instructions, when executed by the user system 112, may cause the display 122 of the user system 112 to present the presentation 214. The presentation 214 can also be transmitted to the database server 126 for storage in the database 128. The user system 112 can access the presentation 214 and instructions to cause display of the presentation 214 via the network 110.

According to some examples, the functionality of the image processing system 132 is incorporated in the local application 114 of the user system 112. Accessing the image processing system 132 through the local application 114 can improve processing speeds by cutting down on network 110 requests. In the event the network 110 is interrupted or the network servers 124 are otherwise unavailable, the application 114 will be able to run the image processing system 132.

According to some examples, the functionality of the image processing system 132 is incorporated in the local application 108 of the image capture system 102. In such instances, functionality prompting re-capture of one or more FAF images 202 can be done in real-time while the patient is present. Fast, automatic, and standardized image processing of the FAF images 202 is used to ensure the FAF images 202 captured by the image capture system 102 are of sufficient quality for use in a clinical setting, such as for diagnostic purposes or in a clinical trial, before the patient leaves the clinical setting. Thereby increasing efficiency and shortening timelines for diagnosing ophthalmic conditions.

It shall be appreciated by those of ordinary skill in the art that the extraction system 204, the gradeability model 206, the quality model 208, and the post-processing system 210 are not necessarily distinct systems and may share functions and processing between one another. Further, the processing performed by each component of the image processing system 132 may not occur in the order of processing depicted in FIG. 2. The interactions between the extraction system 204, the gradeability model 206, the quality model 208, and the post-processing system 210 may be more non-linear than the linear flow depicted in FIG. 2.

Figure 3A:
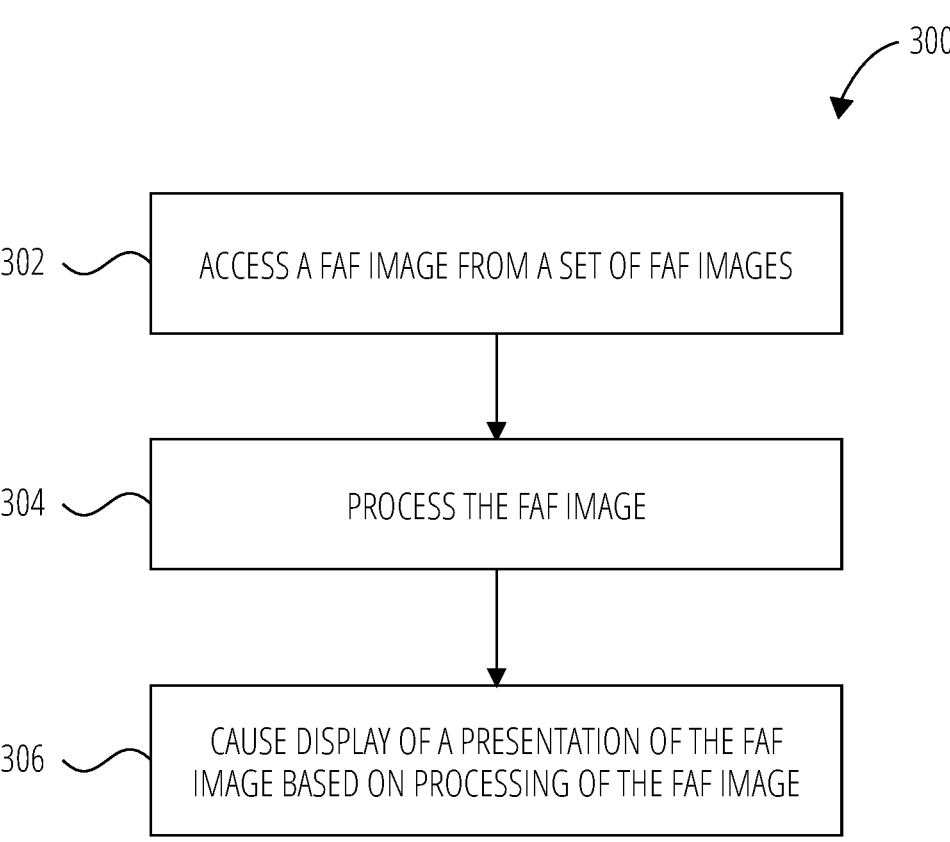
FIG. 3A is a flowchart for a method of FAF image analysis, according to some examples.

FIG. 3A is a flowchart for a method 300 of FAF image analysis, according to some examples. The method 300 can be performed by processing logic that can include hardware (e.g., a processing device, circuitry, dedicated logic, programmable logic, microcode, hardware of a device, an integrated circuit, etc.), software (e.g., instructions run or executed on a processing device), or a combination thereof. In some embodiments, the method 300 is performed by functional components of the system 100. While the operations below are described as being performed by a processing device, it shall be appreciated that the operations of the method 300 may not necessarily be performed by the same processing device. Accordingly, any one or more of the operations of the method 300 can be performed by any one or more of the image capture system 102, the user system 112, the network server system 116, or any combination thereof. The processing device may, for example, be the image processing system 132.

Although shown in a particular sequence or order, unless otherwise specified, the order of the processes can be modified. Thus, the illustrated embodiments should be understood only as examples, and the illustrated processes can be performed in a different order, and some processes can be performed in parallel. Additionally, one or more processes can be omitted in various embodiments. Thus, not all processes are required in every embodiment. Other process flows are possible.

At block 302, the processing device accesses a FAF image from a set of FAF images. The set of FAF images 202 may be accessed, or otherwise received from, a database, such as database 128. Each FAF image in the set of FAF images is of the fundus of an eye of a patient; each FAF image in the set of FAF images is of the same patient, taken on the same day. The FAF images were captured by a clinical imaging apparatus, such as the image capture system 102.

At block 304, the processing device processes the FAF image. The processing of the FAF image analyzes the quality of the FAF image. In particular, processing the FAF image generates image quality data about the FAF image. The processing device may employ one or more artificial neural networks, such as a deep learning model and a machine-learned model, to process the FAF image and generate image quality data. According to some examples, the processing device may perform one or more post-processing functions. The post-processing functions may include generating a presentation of the image quality data, and/or evaluating the image quality data. Processing the FAF image may include one or more sub-operations, discussed in relation to FIG. 3B.

At block 306, the processing device causes display of a presentation of the FAF image based on the processing of the FAF image. The presentation includes the image quality data generated by processing the FAF image at block 304. According to some examples, the presentation is a UI, and the processing device causes display of the presentation on a user device, such as a client device. The processing device causing display of the presentation may include presenting a notification at the client device that includes the presentation.

Figure 3B:
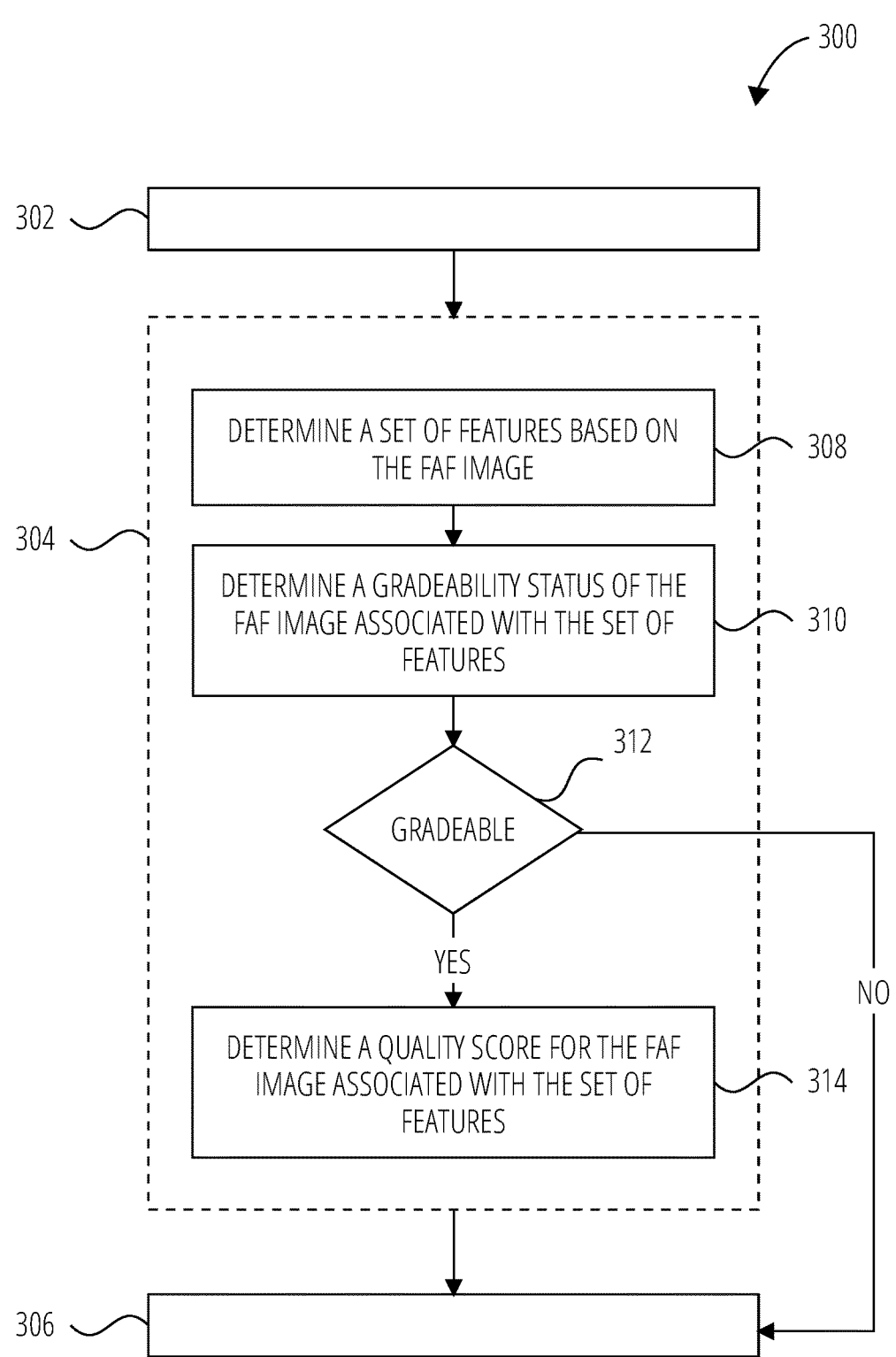
FIG. 3B is a flowchart for a method of FAF image analysis, according to some examples.

FIG. 3B is a flowchart for a method 300 of FAF image analysis, according to some examples. FIG. 3B shows the method 300 may, in some embodiments, further include block 308, block 310, decision block 312, and block 314. Consistent with these embodiments, the block 308, the block 310, the decision block 312, and the block 314 may be performed as part of operation 304 where the processing device processes the FAF image.

At block 308, the processing device determines a set of features based on the FAF image. The set of features can include metadata about the FAF image, a pixel array, a set of local features, and/or a set of global features. Each global feature and each local features in the set of features is based on one or more quality metrics, such as signal intensity, noise, contrast, and blurriness. Each global feature is based on the whole FAF image. Each local feature is based on a patch that represents a subset of the FAF image.

At block 310, the processing device determines a gradeability status of the FAF image associated with the set of features. In particular, the processing device determines the gradeability status based on the set of features. The processing device may modify the set of features in processing the set of features to determine a gradeability status. According to some examples, the processing device applies the set of features to a deep learning model to determine gradeability status. The deep learning model has been trained to perform binary classification of FAF images to determine a gradeability status. The gradeability status is one of gradable or non-gradable.

At decision block 312, the processing device determines whether the FAF image is gradable. In particular, the processing device evaluates the gradeability of the FAF image based on the gradeability status. In instances where the gradeability status is gradable, the method 300 proceeds to block 314. In instances where the gradeability status is non-gradable, the method 300 proceeds to block 306. Non-gradable FAF images are not of sufficient image quality for further analysis. According to some examples, non-gradable images may be discarded rather than proceeding to block 306. According to some examples, non-gradable images may be automatically assigned a quality score of zero without further analysis.

At block 314, the processing device determines a quality score for the FAF image associated with the set of features. In particular, the processing device calculates a quality score based on the set of features. According to some examples, the processing device applies the set of features to a machine-learned model to determine the quality score. The machine-learned model has been trained to determine a quality score for the FAF image associated with the set of features. The machine learned model processes gradable FAF images.

According to some examples consistent with FIG. 3B, at block 306, the presentation generated by the processing device includes the quality score determined at block 314. The presentation may also include the gradeability status determined at block 310. In instances where the FAF image is non-gradable, the presentation may not include a quality score.

Figure 3C:
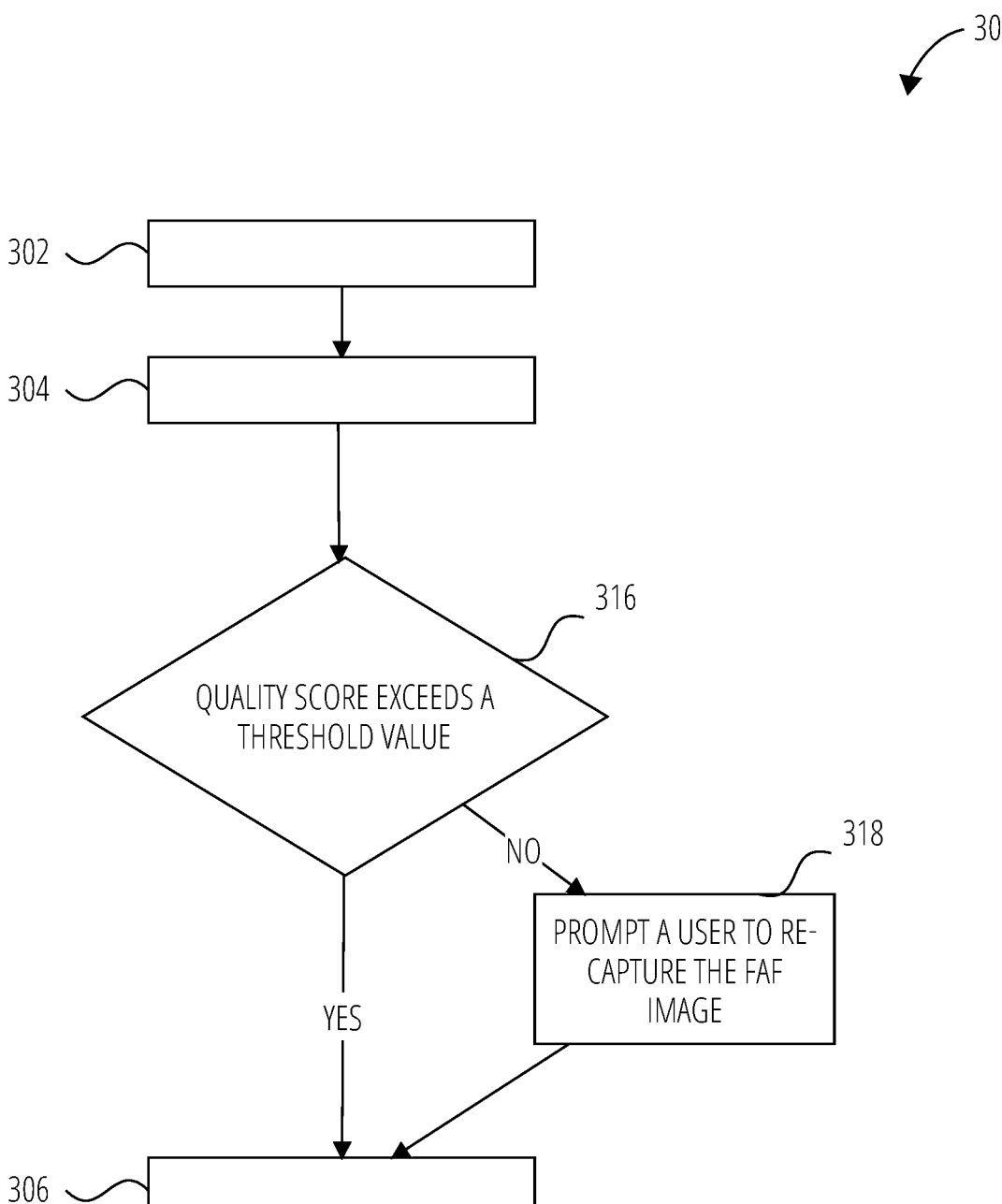
FIG. 3C is a flowchart for a method of FAF image analysis, according to some examples.

FIG. 3C is a flowchart for a method 300 of FAF image analysis, according to some examples. FIG. 3C shows the method 300 may, in some embodiments, further include decision block 316, and block 318. Consistent with these embodiments, the decision block 316, and block 318 may be performed as between block 304, where the processing device processes the FAF image, and block 306, where the processing device causes display of the presentation. Other orders of operation are possible.

At decision block 316, the processing device determines whether the quality score exceeds a threshold value. In particular, the processing device evaluates whether the quality score associated with the FAF image exceeds a predefined threshold value. The processing device may access the threshold value from memory or a database, such as database 128. According to some examples, the evaluation of the quality score is a post-processing function that occurs as part of block 304.

The threshold value may be a threshold quality score, according to some examples. The threshold quality score represents, for example, a minimum image quality for use in clinical settings, such as diagnostic analysis. FAF images with a quality score that exceed the threshold quality score have sufficient image quality for clinical use. In instances where the quality score of the FAF image exceeds the threshold value, the method 300 proceeds to block 306. In instances where the quality score of the FAF image is less than the threshold value, the method 300 proceeds to block 318, according to some examples.

At block 318, the processing device prompts a user to recapture the FAF image responsive to the quality score of the FAF image being less than the threshold value. That is, if the image is not of sufficient quality, then the processing device indicates it should be re-taken. The processing device may prompt the user to recapture the FAF image through a notification sent to a client device of the user. According to some embodiments, the processing device generated the prompt and passes the prompt to block 306.

According to some examples consistent with FIG. 3C, at block 306, the presentation generated by the processing device includes the prompt to re-capture the FAF image in the event the quality score does not exceed the threshold value. For example, the presentation may include the FAF image, the quality score, and an indication of the quality score being less than the threshold quality score. In the event the quality score exceeds the threshold value, the presentation may include an indication that the quality score exceeds the threshold quality score, or otherwise is of sufficient quality for clinical use.

Figure 3D:
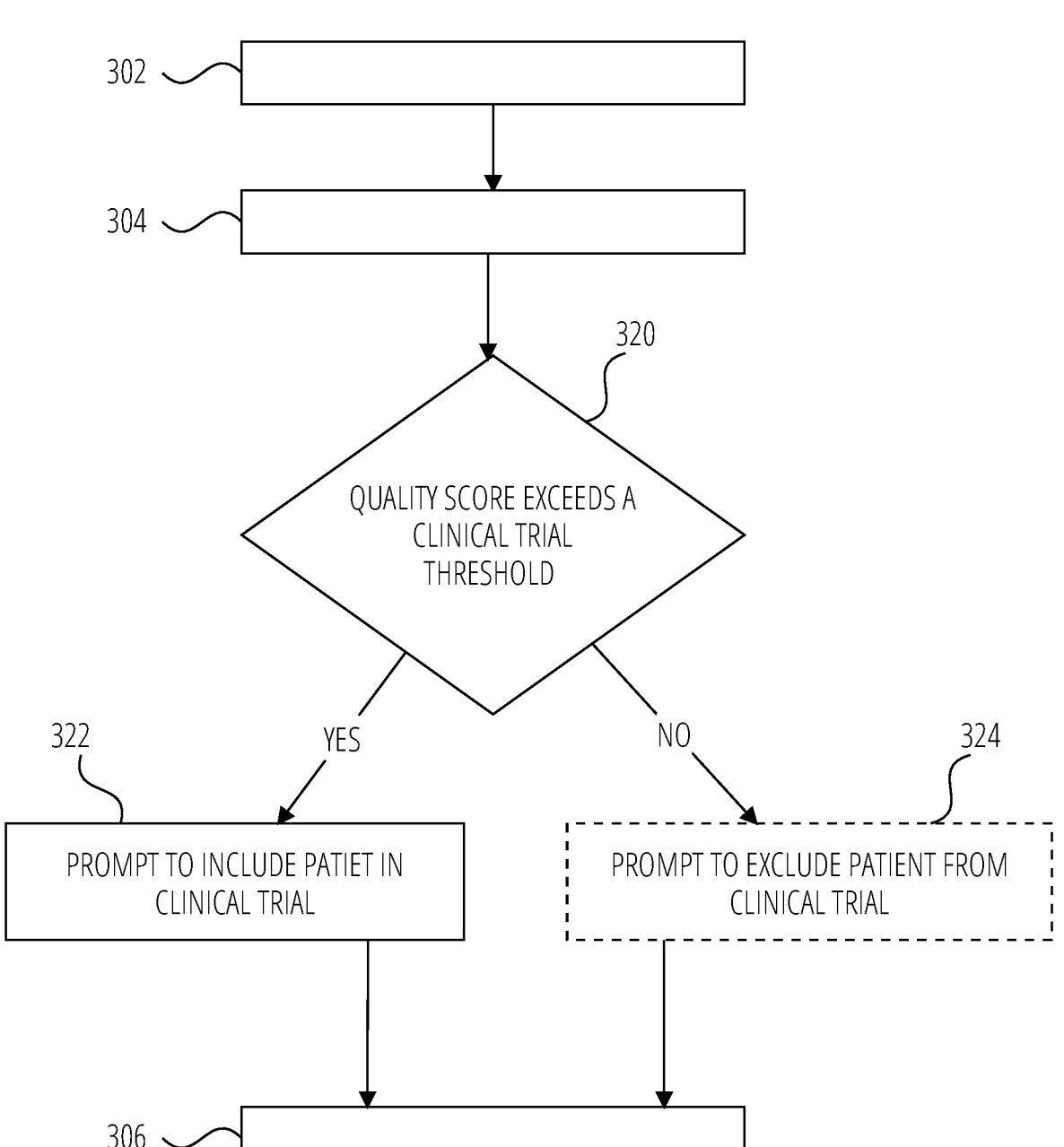
FIG. 3D is a flowchart for a method of FAF image analysis, according to some examples.

FIG. 3D is a flowchart for a method 300 of FAF image analysis, according to some examples. FIG. 3D shows the method 300 may, in some embodiments, further include decision block 320, block 322, and block 324. Consistent with these embodiments, the decision block 320, block 322, and block 324 may be performed as between block 304, where the processing device processes the FAF image, and block 306, where the processing device causes display of the presentation. Other orders of operation are possible.

At decision block 320, the processing device determines whether the quality score exceeds a clinical trial threshold. In particular, the processing device evaluates whether the quality score associated with the FAF image exceeds a predefined clinical trial threshold value. The processing device may access the clinical trial threshold from memory or a database, such as database 128. According to some examples, the evaluation of the quality score is a post-processing function that occurs as part of block 304.

The clinical trial threshold is a value representing minimum image quality for use in a particular clinical trial. The processing device may have access to multiple clinical trial thresholds, each associated with one or more clinical trials. The processing device may repeat evaluations at decision block 320 for each clinical trial threshold.

At block 322, responsive to determining the quality score of the FAF image exceeds a clinical trial threshold, the processing device prompts including the patient associated with the FAF image in the clinical trial associated with the clinical trial threshold. The prompt includes information about the clinical trial, such as the name of the clinical trial, the research area of the clinical trial, and information on enrolling in the clinical trial. According to some embodiments, the processing device generated the prompt and passes the prompt to block 306.

At block 324, optionally, responsive to determining the quality score of the FAF image does not exceed a clinical trial threshold, the processing device prompts excluding the patient associated with the FAF image in the clinical trial associated with the clinical trial threshold. The prompt may include information about the clinical trial. According to some embodiments, the processing device generated the prompt and passes the prompt to block 306.

According to some examples consistent with FIG. 3D, at block 306, the presentation generated by the processing device includes the prompt generated at block 322 or block 324. For example, the presentation may include the FAF image, the quality score, and an indication of the quality score being greater or less than the clinical trial threshold quality score. The presentation may be provided to a clinician and/or the patient.

Figure 4:
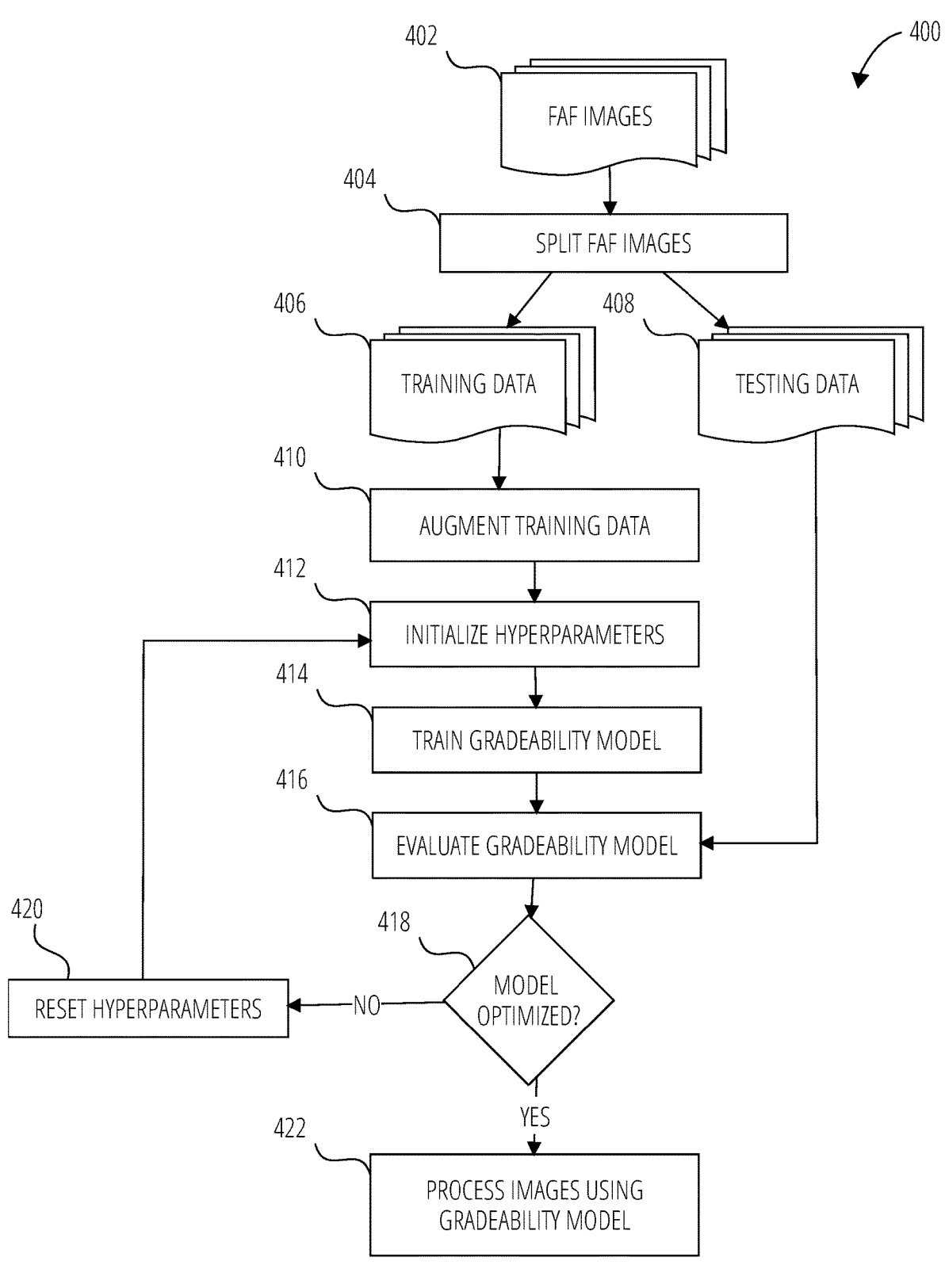
FIG. 4 is a flowchart of a method for training a gradeability model, according to some examples.

FIG. 4 is a flowchart of a method 400 for training a gradeability model, according to some examples. The method 400 can be performed by processing logic that can include hardware (e.g., a processing device, circuitry, dedicated logic, programmable logic, microcode, hardware of a device, an integrated circuit, etc.), software (e.g., instructions run or executed on a processing device), or a combination thereof. In some embodiments, the method 400 is performed by functional components of the system 100.

While the operations below are described as being performed by a processing device, it shall be appreciated that the operations of the method 400 may not necessarily be performed by the same processing device. Accordingly, any one or more of the operations of the method 400 can be performed by any one or more of the image capture system 102, the user system 112, or the network server system 116, or any combination thereof. The processing device may, for example, be the image processing system 132.

Although shown in a particular sequence or order, unless otherwise specified, the order of the processes can be modified. Thus, the illustrated embodiments should be understood only as examples, and the illustrated processes can be performed in a different order, and some processes can be performed in parallel. Additionally, one or more processes can be omitted in various embodiments. Thus, not all processes are required in every embodiment. Other process flows are possible.

The gradeability model trained by the method 400 can determine a gradeability status of a FAF image. The gradeability model is a deep learning model. The gradeability model may be, for example, the gradeability model 206. According to some examples, the gradeability model is implemented as one of an artificial neural network, a convolutional neural network, a feedforward neural network, a recurrent neural network, a deep neural network, or any other type of neural network. The gradeability model may have any number of layers in its network. The method 400 of training the gradeability model may be supervised, semi-supervised, or unsupervised.

In an exemplary embodiment, the gradeability model is implemented as a visual geometry group (VGG) with 19 convolutional layers, so called VGG-19 architecture. VGG-19 is a convolutional neural network architecture for implementing deep learning. The VGG-19 gradeability model uses a rectified linear unit (ReLu) activation function.

The method 400 begins with a set of FAF images 402. The set of FAF images 402 includes one or more images of the fundus of eyes of patients. That is, the set of FAF images 402 includes FAF images 402 from multiple different patients. The set of FAF images 402 may include images of varying imaging quality. For example, the set of FAF images 402 includes both gradable and non-gradable images. The set of FAF images 402 have been manually labeled with results. In this instance, the results are gradable (e.g., assigned 0) or non-gradable (e.g., assigned 1).

In the exemplary embodiment, the set of FAF images 402 includes 550 FAF images 402. Each FAF image in the set of FAF images 402 is 512×512×3 pixels.

At block 404, the processing device splits the set of FAF images 402. In particular, the set of FAF images 402 are split into a training data 406 and a testing data 408. According to some examples, the splitting up of the FAF images 402 is randomized. For example, there may be a predefined fraction or percentage of the set of FAF images 402 to be included in each of the training data 406 and the testing data 408. Additionally, or alternatively, there may be a predefined number of FAF images 402 to be included in each of the training data 406 and the testing data 408. That is, there may be a minimum number of FAF images 402, for example 100 FAF images 402, to be included in the training data 406.

In the exemplary embodiment, the set of 550 FAF images 402 are split at block 404 into a set of 330 FAF images in the training data 406 and 220 FAF images in the testing data 408.

At block 410, the processing device augments the training data 406. Augmenting the training data 406 increases the effective size of the set of training data 406. For example, a FAF image in the training data 406 is subjected to one or more edits, such as image rotation, image inversion, adjustments to image brightness, adjustments to image contrast, and the like. The unedited FAF image and the edited FAF image are both included in the training data 406. Accordingly, the augmentation at block 410 modifies the training data 406.

At block 412, the processing device initialize hyperparameters of the gradeability model. According to some examples, the gradeability model includes parameters and hyperparameters, each of which represent coefficients of the gradeability model. The parameters are, for example, set by the gradeability model in block 414. According to some embodiments, the hyperparameters are initialized by user input. In embodiments wherein the gradeability model does not include hyperparameters, the processing device may skip block 412 in the method 400.

At block 414, the processing device trains the gradeability model. In particular, the processing device uses the training data 406 to train the gradeability model. The gradeability model processes each FAF image in the training data 406 as the inputs and processes each gradeability status (e.g., 0 for gradable, 1 for non-gradable) as the results. In processing the inputs and results, the gradeability model assigns values to its parameters such that the layers of the gradeability model are weighted to achieve the desired result from an input while minimizing loss function and error.

In the exemplary embodiment, training the VGG-19 gradeability model employs a cross-entropy loss function, an Adam's optimizer with a learning rate of 0.0005, and a batch size of 4 FAF images.

At block 416, the processing device evaluates the gradeability model. In particular, the processing device uses the testing data 408 to evaluate the trained gradeability model. The gradeability model processes each FAF image in the testing data 408 as inputs and generates a result (e.g., 0 for gradable, 1 for non-gradable) based on the input.

At decision block 418, the processing device determines whether the gradeability model is optimized. According to some examples, the generated result is compared to the manually labeled result to determine accuracy of the gradeability model. If the accuracy is sufficiently high (e.g., above a threshold accuracy), the gradeability model is optimized. In the event of supervised or semi-supervised training, the training can be terminated based on additional or alternative criteria being met.

In the exemplary embodiment as described herein, the trained gradeability model yields an accuracy of 92.0%.

In the event the processing device determines the gradeability model is not optimized, the method 400 proceeds to block 420. At block 420, the processing device resets the hyperparameters. According to some examples, the parameters may also be reset. Following block 420, the method 400 proceeds to the block 412 to initialize hyperparameters again.

In the event the processing device determines the gradeability model is optimized, the method 400 proceeds to block 422. At block 422, the processing device is able to process FAF images using the gradeability model. For example, the processing device may proceed with method 300 to analyze FAF images.

Figure 5A:
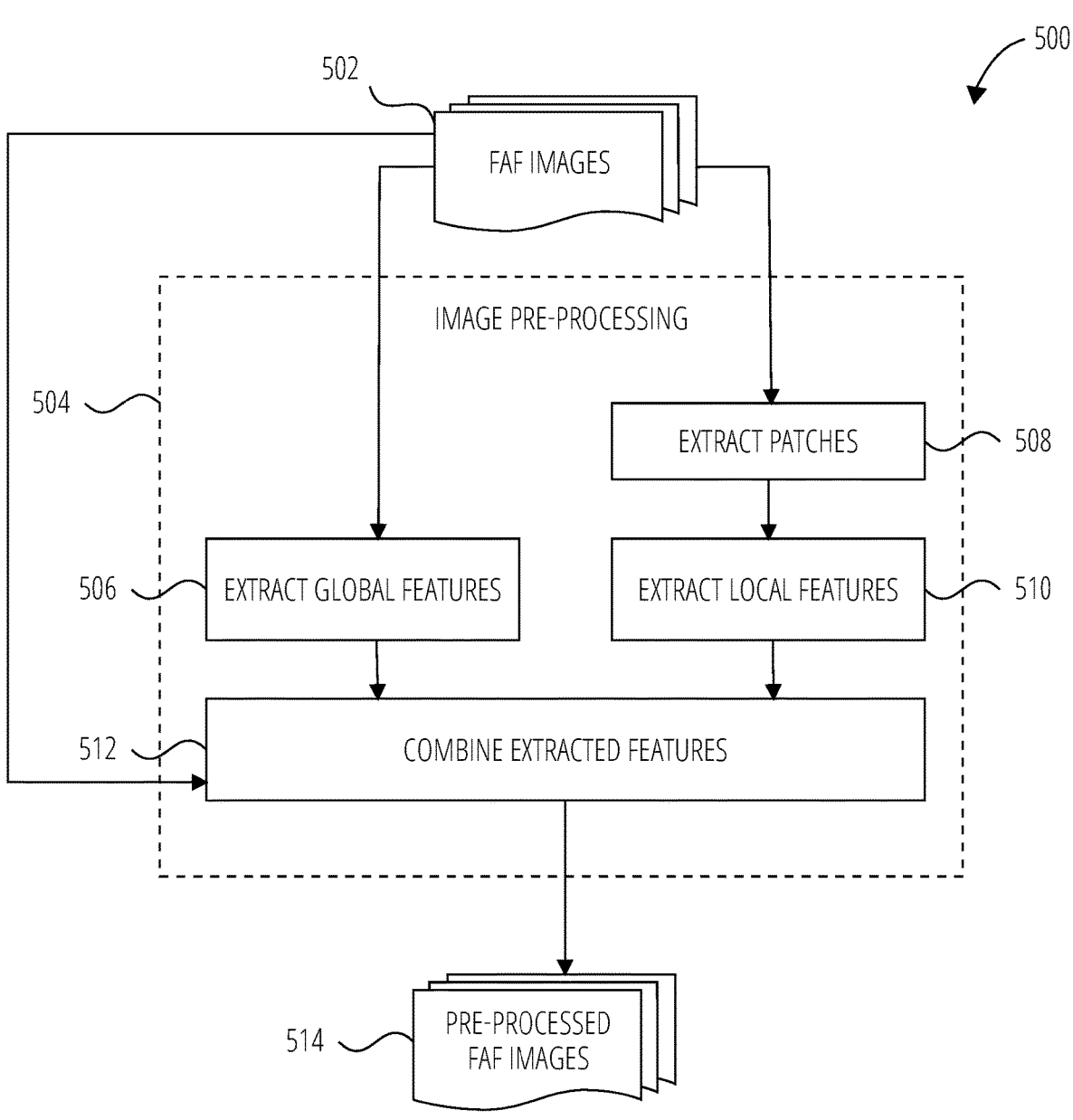
FIG. 5A is a flowchart of a method for training a quality model, according to some examples.

FIG. 5A is a flowchart of a method 500 for training a quality model, according to some examples. The method 500 can be performed by processing logic that can include hardware (e.g., a processing device, circuitry, dedicated logic, programmable logic, microcode, hardware of a device, an integrated circuit, etc.), software (e.g., instructions run or executed on a processing device), or a combination thereof. In some embodiments, the method 500 is performed by functional components of the system 100. While the operations below are described as being performed by a processing device, it shall be appreciated that the operations of the method 500 may not necessarily be performed by the same processing device. Accordingly, any one or more of the operations of the method 500 can be performed by any one or more of the image capture system 102, the user system 112, or the network server system 116, or any combination thereof. The processing device may, for example, be the image processing system 132.

Although shown in a particular sequence or order, unless otherwise specified, the order of the processes can be modified. Thus, the illustrated embodiments should be understood only as examples, and the illustrated processes can be performed in a different order, and some processes can be performed in parallel. Additionally, one or more processes can be omitted in various embodiments. Thus, not all processes are required in every embodiment. Other process flows are possible.

The quality model trained by the method 500 can determine a quality score of a FAF image. The gradeability model is a machine-learned model. The gradeability model may be, for example, the quality model 208. According to some examples, the quality model is implemented as one of a neural network (of any type), a decision tree, a support-vector machine, a regression analysis model, a Bayesian network, a Gaussian process, or any other type of machine-learned model. The quality model may have any number of layers. The method 500 of training the quality model may be supervised, semi-supervised, or unsupervised.

According to an exemplary embodiment, the quality model is implemented as a support-vector regressor (SVR) model.

The method 500 begins with a set of FAF images 502. The set of FAF images 502 includes one or more images of the fundus of eyes of patients. That is, the set of FAF images 502 includes FAF images 502 from multiple different patients. The set of FAF images 502 may include images of varying imaging quality. For example, the set of FAF images 502 includes high quality images, medium quality images, and low-quality images. The set of FAF images 502 have been manually labeled with results. In this instance, the results are a quality score.

In the exemplary embodiment, the set of FAF images 502 includes 550 FAF images 502. Each FAF image in the set of FAF images 502 is 512×512×3 pixels. The FAF images 502 are manually assigned quality scores on a scale of 1-5. Scores of 1 or 2 indicate poor image quality. Scores of 3-5 indicate medium to high quality, with a score of 5 representing the highest quality.

At block 504, the processing device provides image pre-processing. The image pre-processing is one or more operations prior to providing the FAF images 502 to the quality model. According to some examples, the set of FAF images 502 are duplicated. One copy of the set of FAF images 502 is provided to block 506 for pre-processing; the other set of FAF images 502 is provided to block 508 for pre-processing.

At block 506, the processing device extracts global features from the set of FAF images 502. Each global feature represents one or more quality metrics of a FAF image as a whole. The one or more quality metrics include one or more of the list comprising signal intensity, noise, contrast, and blurriness. Extracting (e.g., deriving from the pixels that compose the FAF image) global features is less computationally intense than extracting local features.

At block 508, the processing device extracts patches from the set of FAF images 502. Each patch represents a section of the FAF image. For example, a patch is a submatrix of pixels of the matrix of pixels that make up the FAF image. Each patch may vary in size, and patches may overlap one another. According to some examples, at least some patches are extracted by identifying portions of the FAF image that contain identifiable anatomical structures, such as optical disc, macula, and vascular network(s).

At block 510, the processing device extracts local features from the set of FAF images 502. More specifically, local features are extracted from the patches of a FAF image. Each local feature represents one or more quality metrics of the patch from which it was extracted. Extracting local features is more complex than extracting global features, and more prone to error.

At block 512, the processing device combines all features. That is, the processing device generates a set of features that represents a particular FAF image from the set of FAF images 502. The set of features includes all global features and all local features extracted from the particular FAF image.

In the exemplary embodiment, 22 total features are extracted from each FAF image in the set of FAF images 502. Of the 22 total features, 18 are local features and 4 are global features. In the exemplary embodiment, packages such as scikit-learn, scikit-image, and numpy are used to compute quality metrics for each feature. For example, the packages are used to compute the 25th quantile, 50th quantile, and 75th quantile of the quality metrics for each patch to generate each local feature. Similarly, packages are used to compute the 10th quantile, 50th quantile, and 90th quantile of each FAF image to generate each global feature.

Further at block 512, the processing device combines the combined set of features with the FAF images 502 to generate pre-processed FAF images 514.

Figure 5B:
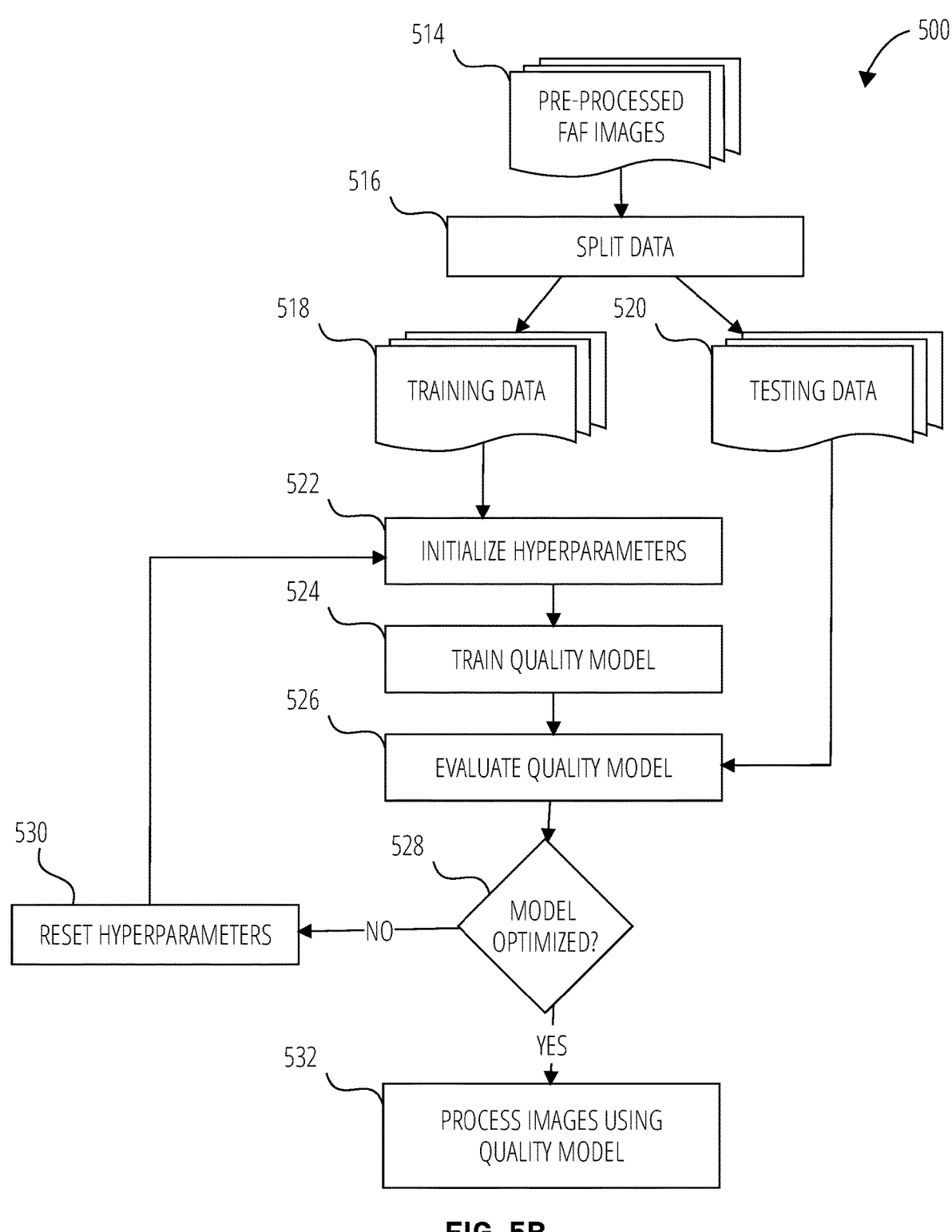
FIG. 5B is a flowchart of a method for training a quality model, according to some examples.

FIG. 5B is a flowchart of a method 500 for training a quality model, according to some examples. The method 500 continues with the pre-processed FAF images 514.

At block 516, the processing device splits the pre-processed FAF images 514. In particular, the set of pre-processed FAF images 514 are split into a training data 518 and a testing data 520. According to some examples, the splitting up of the pre-processed FAF images 514 is randomized. For example, there may be a predefined fraction or percentage of the set of pre-processed FAF images 514 to be included in each of the training data 518 and the testing data 520. Additionally, or alternatively, there may be a predefined number of pre-processed FAF images 514 to be included in each of the training data 518 and the testing data 520. That is, there may be a minimum number of pre-processed FAF images 514, for example 100 pre-processed FAF images 514, to be included in the training data 518.

In the exemplary embodiment, the set of 550 pre-processed FAF images 514 are split at block 516 into a set of 330 pre-processed FAF images in the training data 518 and 220 pre-processed FAF images in the testing data 520.

At block 522, the processing device initialize hyperparameters of the quality model. According to some examples, the quality model includes parameters and hyperparameters, each of which represent coefficients of the quality model. The parameters are, for example, set by the quality model in block 524. According to some embodiments, the hyperparameters are initialized by user input. In embodiments wherein the quality model does not include hyperparameters, the processing device may skip block 522 in the method 500.

At block 524, the processing device trains the quality model. In particular, the processing device uses the training data 518 to train the quality model. The quality model processes each pre-processed FAF image in the training data 518 as the inputs and processes the associated features in the set of features and associated quality score (e.g., score from 1-5) as the results. In processing the inputs and results, the quality model assigns values to its parameters such that the layers of the quality model are weighted to achieve the desired result from an input while minimizing loss function and error.

At block 526, the processing device evaluates the quality model. In particular, the processing device uses the testing data 520 to evaluate the trained quality model. The quality model processes each FAF image in the testing data 520 as inputs and generates a result (e.g., quality score from 1-5) based on the input.

In the exemplary embodiment as described herein, evaluating the quality model includes calculating a mean squared error (MSE) and an r-squared value. Further, cross-validation is used to select the best (e.g., optimized) hyperparameter tuning. In particular, a thrice repeated 5-fold cross validation is used to determine the optimized quality model.

At decision block 528, the processing device determines whether the quality model is optimized. According to some examples, the generated result is compared to the manually labeled result to determine accuracy of the quality model. If the accuracy is sufficiently high (e.g., above a threshold accuracy), the quality model is optimized. In the event of supervised or semi-supervised training, the training can be terminated based on additional or alternative criteria being met.

In the exemplary embodiment as described herein, the optimal trained SVR quality model yields a means-tested MSE of 0.486, with a standard deviation of 0.039, and a mean-tested r-squared value of 0.693, with a standard deviation of 0.030.

In the event the processing device determines the quality model is not optimized, the method 500 proceeds to block 530. At block 530, the processing device resets the hyperparameters. According to some examples, the parameters may also be reset. Following block 530, the method 500 proceeds to the block 522 to initialize hyperparameters again.

In the event the processing device determines the quality model is optimized, the method 500 proceeds to block 532. At block 532, the processing device is able to process features of a FAF image using the quality model. For example, the processing device may proceed with method 300 to analyze FAF images.

Figure 6:
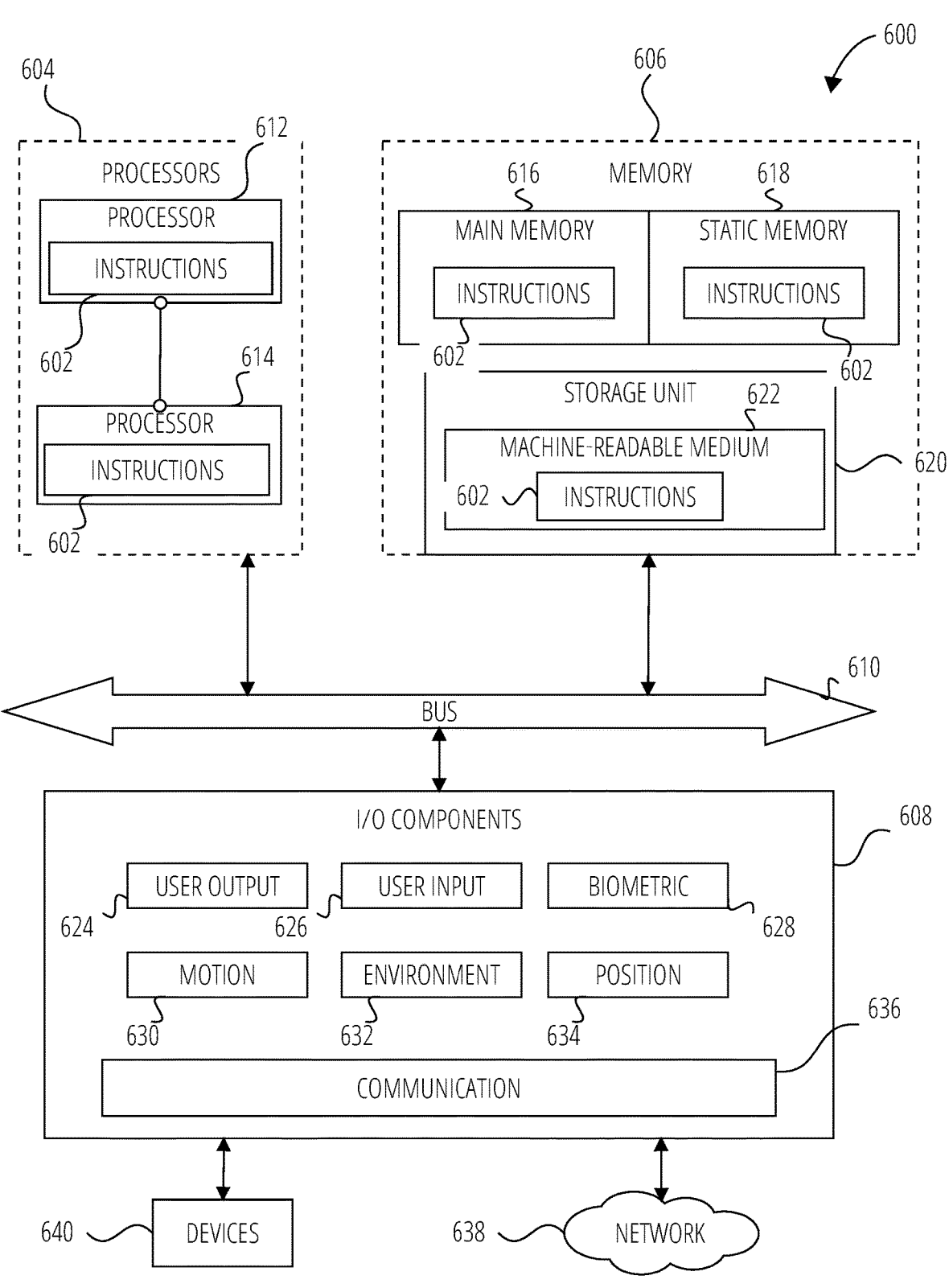
FIG. 6 is a diagrammatic representation of a machine in the form of a computer system within which a set of instructions may be executed to cause the machine to perform any one or more of the methodologies discussed herein, according to some examples.

FIG. 6 is a diagrammatic representation of the machine 600 within which instructions 602 (e.g., software, a program, an application, an applet, an app, or other executable code) for causing the machine 600 to perform any one or more of the methodologies discussed herein may be executed. For example, the instructions 602 may cause the machine 600 to execute any one or more of the methods described herein. The instructions 602 transform the general, non-programmed machine 600 into a particular machine 600 programmed to carry out the described and illustrated functions in the manner described. The machine 600 may operate as a standalone device or may be coupled (e.g., networked) to other machines. In a networked deployment, the machine 600 may operate in the capacity of a server machine or a client machine in a server-client network environment, or as a peer machine in a peer-to-peer (or distributed) network environment. The machine 600 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smartphone, a mobile device, a wearable device (e.g., a smartwatch), a smart home device (e.g., a smart appliance), other smart devices, a web appliance, a network router, a network switch, a network bridge, or any machine capable of executing the instructions 602, sequentially or otherwise, that specify actions to be taken by the machine 600. Further, while a single machine 600 is illustrated, the term "machine" shall also be taken to include a collection of machines that individually or jointly execute the instructions 602 to perform any one or more of the methodologies discussed herein. The machine 600, for example, may comprise the user system 112 or any one of multiple server devices forming part of the network server system 116. In some examples, the machine 600 may also comprise both client and server systems, with certain operations of a particular method or algorithm being performed on the server-side and with certain operations of the particular method or algorithm being performed on the client-side.

The machine 600 may include processors 604, memory 606, and input/output I/O components 608, which may be configured to communicate with each other via a bus 610. In an example, the processors 604 (e.g., a Central Processing Unit (CPU), a Reduced Instruction Set Computing (RISC) Processor, a Complex Instruction Set Computing (CISC) Processor, a Graphics Processing Unit (GPU), a Digital Signal Processor (DSP), an Application Specific Integrated Circuit (ASIC), a Radio-Frequency Integrated Circuit (RFIC), another processor, or any suitable combination thereof) may include, for example, a processor 612 and a processor 614 that execute the instructions 602. The term "processor" is intended to include multi-core processors that may comprise two or more independent processors (sometimes referred to as "cores") that may execute instructions contemporaneously. Although FIG. 6 shows multiple processors 604, the machine 600 may include a single processor with a single core, a single processor with multiple cores (e.g., a multi-core processor), multiple processors with a single core, multiple processors with multiples cores, or any combination thereof.

The memory 606 includes a main memory 616, a static memory 618, and a storage unit 620, both accessible to the processors 604 via the bus 610. The main memory 606, the static main memory 616, and storage unit 620 store the instructions 602 embodying any one or more of the methodologies or functions described herein. The instructions 602 may also reside, completely or partially, within the main memory 616, within the static memory 618, within machine-readable medium 622 within the storage unit 620, within at least one of the processors 604 (e.g., within the processor's cache memory), or any suitable combination thereof, during execution thereof by the machine 600.

The I/O components 608 may include a wide variety of components to receive input, provide output, produce output, transmit information, exchange information, capture measurements, and so on. The specific I/O components 608 that are included in a particular machine will depend on the type of machine. For example, portable machines such as mobile phones may include a touch input device or other such input mechanisms, while a headless server machine will likely not include such a touch input device. It will be appreciated that the I/O components 608 may include many other components that are not shown in FIG. 6. In various examples, the I/O components 608 may include user output components 624 and user input components 626. The user output components 624 may include visual components (e.g., a display such as a plasma display panel (PDP), a light-emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The user input components 626 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and force of touches or touch gestures, or other tactile input components), audio input components (e.g., a microphone), and the like.

In further examples, the I/O components 608 may include biometric components 628, motion components 630, environmental components 632, or position components 634, among a wide array of other components. For example, the biometric components 628 include components to detect expressions (e.g., hand expressions, facial expressions, vocal expressions, body gestures, or eye-tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The motion components 630 include acceleration sensor components (e.g., accelerometer), gravitation sensor components, rotation sensor components (e.g., gyroscope).

The environmental components 632 include, for example, one or cameras (with still image/photograph and video capabilities), illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment.

With respect to cameras, the user system 1122 may have a camera system comprising, for example, front cameras on a front surface of the user system 112 and rear cameras on a rear surface of the user system 112. The front cameras may, for example, be used to capture still images and video of a user of the user system 112 (e.g., "selfies"), which may then be augmented with augmentation data (e.g., filters) described above. The rear cameras may, for example, be used to capture still images and videos in a more traditional camera mode, with these images similarly being augmented with augmentation data. In addition to front and rear cameras, the user system 112 may also include a 360° camera for capturing 360° photographs and videos.

Further, the camera system of the user system 112 may include dual rear cameras (e.g., a primary camera as well as a depth-sensing camera), or even triple, quad or penta rear camera configurations on the front and rear sides of the user system 112. These multiple cameras systems may include a wide camera, an ultra-wide camera, a telephoto camera, a macro camera, and a depth sensor, for example.

The position components 634 include location sensor components (e.g., a GPS receiver components), altitude sensor components (e.g., altimeters or barometers that detect air pressure from which altitude may be derived), orientation sensor components (e.g., magnetometers), and the like.

Communication may be implemented using a wide variety of technologies. The I/O components 608 further include communication components 636 operable to couple the machine 600 to a network 638 or devices 640 via respective coupling or connections. For example, the communication components 636 may include a network interface component or another suitable device to interface with the network 638. In further examples, the communication components 636 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 640 may be another machine or any of a wide variety of peripheral devices (e.g., a peripheral device coupled via a USB).

Moreover, the communication components 636 may detect identifiers or include components operable to detect identifiers. For example, the communication components 636 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 636, such as location via Internet Protocol (IP) geolocation, location via Wi-Fi® signal triangulation, location via detecting an NFC beacon signal that may indicate a particular location, and so forth.

The various memories (e.g., main memory 616, static memory 618, and memory of the processors 604) and storage unit 620 may store one or more sets of instructions and data structures (e.g., software) embodying or used by any one or more of the methodologies or functions described herein. These instructions (e.g., the instructions 602), when executed by processors 604, cause various operations to implement the disclosed examples.

The instructions 602 may be transmitted or received over the network 6388, using a transmission medium, via a network interface device (e.g., network interface component(s) included in the communication components 636) and using any one of several well-known transfer protocols (e.g., hypertext transfer protocol (HTTP)). Similarly, the instructions 602 may be transmitted or received using a transmission medium via a coupling (e.g., a peer-to-peer coupling) to the devices 640.

Reference throughout this specification to "one embodiment" or "an embodiment" means that a particular feature, structure, or characteristic described in connection with the embodiment is included in at least one embodiment of claimed subject matter. Thus, the appearances of the phrase "in one embodiment" or "an embodiment" in various places throughout this specification are not necessarily all referring to the same embodiment. Furthermore, the particular features, structures, or characteristics may be combined in one or more embodiments.

What is claimed is:

1. A system comprising:
   one or more processors of a machine; and
   a memory storing instructions that, when executed by the one or more processors, cause the machine to perform operations comprising:
   accessing a fundus autofluorescence (FAF) image from among a set of FAF images, the FAF image among the set of FAF images comprising a depiction of at least a portion of an eye of a patient;
   processing the FAF image from among the set of FAF images, wherein processing the FAF image comprises:
   determining a set of features based on the FAF image,
   applying the set of features to a deep learning model responsive to the generating the set of features based on the FAF image, wherein the deep learning model has been trained to determine a gradeability status of the FAF image the set of features, and
   applying the set of features to a machine-learned (ML) model based on the gradeability status, the ML model providing a quality score for the FAF image associated with the set of features; and
   responsive to processing the FAF image from among the set of FAF images, causing display of a presentation of the FAF image based on the processing of the FAF image.

2. The system of claim 1, wherein causing the display of the presentation of the FAF image further comprises:
   determining the quality score exceeds a threshold value; and
   presenting a notification at a client device responsive to the determining the score exceeds the threshold value.

3. The system of claim 2, the operations further comprising:
   determining a ranking of the FAF image among the set of FAF images based on the quality score; and
   presenting the FAF image at a position among the set of FAF images based on the ranking.

4. The system of claim 2, wherein the threshold value is a clinical trial threshold quality score associated with a clinical trial, further comprising:
   prompting the user of the client device to include the patient in the clinical trial.

5. The system of claim 1, the operations further comprising:
   determining the quality score of the FAF image is less than a threshold quality score; and
   prompting the user of the client device to re-capture the FAF image.

6. The system of claim 1, wherein the gradeability status of the FAF image is one of gradable or non-gradable.

7. The system of claim 6, wherein processing the FAF image further comprises:
   responsive to determining the gradeability status of the FAF image is non-gradable, removing the image from the set of FAF images.

8. The system of claim 1, wherein determining the set of features based on the FAF image comprises:

determining a set of global features based on the FAF image, each global feature in the set of global features being based on one or more quality metrics of the FAF image;

determining a set of patches, each patch comprising a portion of the FAF image;

determining a set of local features based on the set of patches, each local feature in the set of local features being based on one or more quality metrics of a patch in the set of patches; and determining the set of features, the set of features including the set of global features and the set of local features.

9. The system of claim 8, wherein determining the set of patches is based at least in part on identifying one or more anatomical structures in the FAF image.

10. A method comprising:

accessing a fundus autofluorescence (FAF) image from among a set of FAF images, the FAF image among the set of FAF images comprising a depiction of at least a portion of an eye of a patient;

processing the FAF image from among the set of FAF images, wherein processing the FAF image comprises:

determining a set of features based on the FAF image, applying the set of features to a deep learning model responsive to the generating the set of features based on the FAF image, wherein the deep learning model has been trained to determine a gradeability status of the FAF image the set of features, and applying the set of features to a machine-learned (ML) model based on the gradeability status, the ML model providing a quality score for the FAF image associated with the set of features; and responsive to processing the FAF image from among the set of FAF images, causing display of a presentation of the FAF image based on the processing of the FAF image.

11. The method of claim 10, wherein causing the display of the presentation of the FAF image further comprises:

determining the quality score exceeds a threshold value; and presenting a notification at a client device responsive to the determining the score exceeds the threshold value.

12. The method of claim 11, further comprising:

determining a ranking of the FAF image among the set of FAF images based on the quality score; and presenting the FAF image at a position among the set of FAF images based on the ranking.

13. The method of claim 11, wherein the threshold value is a clinical trial threshold quality score associated with a clinical trial, further comprising:

prompting the user of the client device to include the patient in the clinical trial.

14. The method of claim 10, further comprising:

determining the quality score of the FAF image is less than a threshold quality score; and prompting the user of the client device to re-capture the FAF image.

15. The method of claim 10, wherein the gradeability status of the FAF image is one of gradable or non-gradable.

16. The method of claim 15, wherein processing the FAF image further comprises:

responsive to determining the gradeability status of the FAF image is non-gradable, removing the image from the set of FAF images.

17. The method of claim 10, wherein determining the set of features based on the FAF image comprises:

determining a set of global features based on the FAF image, each global feature in the set of global features being based on one or more quality metrics of the FAF image;

determining a set of patches, each patch comprising a portion of the FAF image;

determining a set of local features based on the set of patches, each local feature in the set of local features being based on one or more quality metrics of a patch in the set of patches; and determining the set of features, the set of features including the set of global features and the set of local features.

18. The method of claim 17, wherein determining the set of patches is based at least in part on identifying one or more anatomical structures in the FAF image.

19. A non-transitory computer-readable storage medium, the computer-readable storage medium including instructions that when executed by a computer, cause the computer to:

access a fundus autofluorescence (FAF) image from among a set of FAF images, the FAF image among the set of FAF images comprising a depiction of at least a portion of an eye of a patient;

process the FAF image from among the set of FAF images, wherein processing the FAF image comprises:

determine a set of features based on the FAF image, apply the set of features to a deep learning model responsive to the generating the set of features based on the FAF image, wherein the deep learning model has been trained to determine a gradeability status of the FAF image the set of features, and apply the set of features to a machine-learned (ML) model based on the gradeability status, the ML model providing a quality score for the FAF image associated with the set of features; and responsive to processing the FAF image from among the set of FAF images, cause display of a presentation of the FAF image based on the processing of the FAF image.

20. The non-transitory computer readable storage medium of claim 19, wherein determining the set of features based on the FAF image comprises:

determining a set of global features based on the FAF image, each global feature in the set of global features being based on one or more quality metrics of the FAF image;

determining a set of patches, each patch comprising a portion of the FAF image;

determining a set of local features based on the set of patches, each local feature in the set of local features being based on one or more quality metrics of a patch in the set of patches; and determining the set of features, the set of features including the set of global features and the set of local features.

* * * * *